United States Patent
Grubis

(10) Patent No.: US 10,021,657 B2
(45) Date of Patent: Jul. 10, 2018

(54) RADIO FREQUENCY IDENTIFICATION MODES IN PATIENT MONITORING

(71) Applicant: General Electric Company, Schenectady, NY (US)

(72) Inventor: Matthew George Grubis, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/692,941

(22) Filed: Aug. 31, 2017

(65) Prior Publication Data

US 2018/0007639 A1    Jan. 4, 2018

Related U.S. Application Data

(63) Continuation of application No. 14/559,236, filed on Dec. 3, 2014.

(51) Int. Cl.
| | |
|---|---|
| *H04W 52/32* | (2009.01) |
| *H04W 52/02* | (2009.01) |
| *H04W 52/34* | (2009.01) |
| *H04W 52/48* | (2009.01) |
| *H04W 12/02* | (2009.01) |

(Continued)

(52) U.S. Cl.
CPC ......... *H04W 52/322* (2013.01); *A61B 5/0024* (2013.01); *G06K 19/00* (2013.01); *H04L 67/12* (2013.01); *H04W 4/008* (2013.01); *H04W 4/021* (2013.01); *H04W 4/80* (2018.02); *H04W 52/0241* (2013.01); *H04W 52/0245* (2013.01); *H04W 52/0251* (2013.01); *H04W 52/34* (2013.01); *H04W 52/48* (2013.01); *A61B 5/01* (2013.01); *A61B 5/02416* (2013.01); *A61B 5/0402* (2013.01); *A61B 5/7405* (2013.01); *A61B 2505/01* (2013.01); *A61B 2505/03* (2013.01); *A61B 2560/0266* (2013.01); *A61B 2562/08* (2013.01); *G06K 2017/009* (2013.01); *H04B 5/0062* (2013.01); *H04W 12/02* (2013.01); *Y02B 60/50* (2013.01); *Y02D 70/00* (2018.01); *Y02D 70/142* (2018.01);

(Continued)

(58) Field of Classification Search
CPC .......... H04W 52/322; H04W 52/0241; H04W 52/0245; H04W 52/0251; H04W 52/34; H04W 4/021; H04W 4/008; H04W 52/48; H04W 12/02; H04L 67/12; G06K 19/00; A61B 5/0024; A61B 2560/0266; A61B 5/7405; A61B 2505/03; A61B 5/01; A61B 5/02416; A61B 2562/08; A61B 5/0402; H04B 5/0062
See application file for complete search history.

(56) References Cited

U.S. PATENT DOCUMENTS

| | | |
|---|---|---|
| 2007/0039039 A1 | 2/2007 | Gilbert |
| 2010/0060425 A1 | 3/2010 | Rodriguez |

(Continued)

*Primary Examiner* — Walter J Divito
(74) *Attorney, Agent, or Firm* — Andrus Intellectual Property Law, LLP

(57) ABSTRACT

Techniques for wireless component monitoring are described herein. The techniques may include entering a low power mode to associate a radio frequency identification (RFID) component with a patient monitoring device within a first range. The techniques also include entering a high power mode wherein the patient monitoring device is to detect the RFID component within a second range of the patient monitoring device, wherein the second range is larger than the first range.

20 Claims, 6 Drawing Sheets

(51) Int. Cl.
  *H04W 4/80* (2018.01)
  *H04W 4/021* (2018.01)
  *H04L 29/08* (2006.01)
  *H04B 5/00* (2006.01)
  *G06K 19/00* (2006.01)
  *G06K 17/00* (2006.01)
  *A61B 5/00* (2006.01)
  *A61B 5/01* (2006.01)
  *A61B 5/024* (2006.01)
  *A61B 5/0402* (2006.01)
  *H04W 4/00* (2018.01)

(52) U.S. Cl.
  CPC .......... *Y02D 70/144* (2018.01); *Y02D 70/162* (2018.01); *Y02D 70/166* (2018.01); *Y02D 70/42* (2018.01)

(56) References Cited

U.S. PATENT DOCUMENTS

| | | |
|---|---|---|
| 2014/0192206 A1 | 7/2014 | Holz |
| 2014/0247156 A1 | 9/2014 | Proud |
| 2014/0249853 A1 | 9/2014 | Proud et al. |
| 2015/0116144 A1 | 4/2015 | Serrano Olmedo |

100

300

400

RADIO FREQUENCY IDENTIFICATION MODES IN PATIENT MONITORING

CROSS REFERENCE TO RELATED APPLICATION

This application is a continuation of U.S. patent application Ser. No. 14/559,236, filed Dec. 3, 2014, which is incorporated herein by reference in entirety.

BACKGROUND OF THE INVENTION

The subject matter disclosed herein relates generally to techniques for wireless component medical monitoring. In medical monitoring, health parameters of a patient may be monitored. Examples of health parameters that may be monitored may include electrocardiograph (ECG) data, blood oxygen saturation, blood pressure, patient temperature, and the like. Each health parameter may be acquired by one or more health acquisition devices configured to gather data for each parameter. Health acquisition devices configured to gather data may be wired to a computerized patient monitoring device on or nearby the patient. In some cases, the health acquisition devices may be configured to wirelessly communicate with the patient monitoring device.

BRIEF DESCRIPTION OF THE INVENTION

An embodiment relates to a method for wireless component monitoring. The method includes entering a low power mode to associate a radio frequency identification (RFID) component with a patient monitoring device within a first range. The method may also include entering a high power mode wherein the patient monitoring device is to detect the RFID component within a second range of the patient monitoring device, wherein the second range is larger than the first range.

Another embodiment relates to a system for wireless component monitoring. The system includes a radio frequency identification (RFID) reader to associate a RFID component a patient monitoring device. The system includes a RFID operation module to operate the patient monitoring device in modes including a low power mode and a high power mode. The low power mode associates the RFID component with the patient monitoring device in a first range. In the high power mode, the patient monitoring device is to detect the RFID component within a second range of the patient monitoring device, wherein the second range is larger than the first range.

Still another embodiment relates to a computer-readable medium for wireless component monitoring. The computer-readable medium includes processor-executable code to enter a low power mode to associate a radio frequency identification (RFID) component with a patient via a patient monitoring device within a first range. The processor-executable code is also configured to enter a high power mode wherein the patient monitoring device is to detect the RFID component within a second range of the computerized patient monitor.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION OF THE INVENTION

Figure 1:
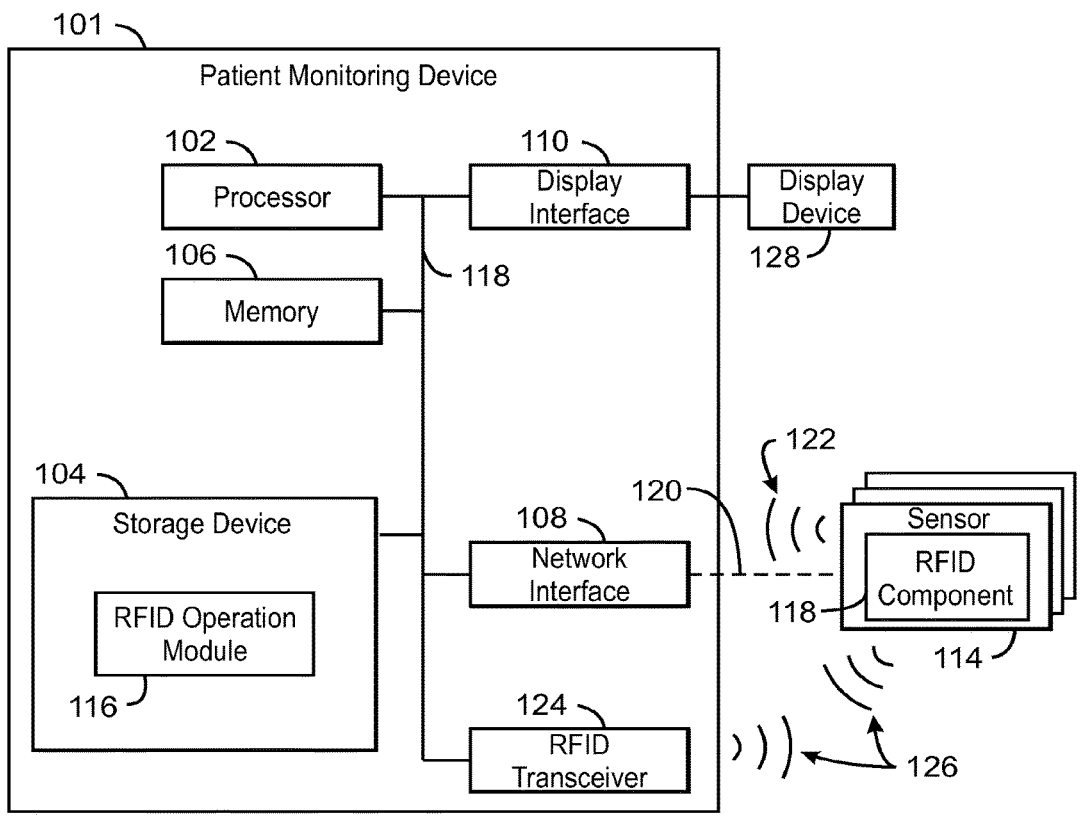
FIG. 1 illustrates a block diagram illustrating a computing system configured to monitor wireless components.

In the following detailed description, reference is made to the accompanying drawings that form a part hereof, and in which is shown by way of illustration of specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the embodiments described herein.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

Various embodiments provide techniques for wireless component monitoring are described herein. A wireless component, as described herein, refers to a radio frequency identification (RFID) component. An RFID component may be embedded into a health data acquisition device used to collect data relating to a health parameter of a patient. A health acquisition device may be referred to generally herein as a sensor.

A patient monitoring device is a computing device configured to communicate with one or more sensors. In some cases, a sensor may be lost or misplaced. In other cases, a sensor communicating with a first patient monitoring device for a first patient, may be erroneously attached to a neighboring patient wherein data related the neighboring patient will be inaccurately recorded for the first patient. For example, an ECG sensor may be dropped from a first patient and placed on a second patient. If the second patient goes into cardiac arrest, a medical technician may erroneously use an artificial defibrillator on the first patient who may or may not be in cardiac arrest, while ignoring the second patient who is in cardiac arrest.

The techniques described herein include a patient monitoring system that is configured to associate a given sensor having a RFID component with the patient monitoring system in a low power mode at a first range. In a high power mode the patient monitoring system is to detect RFID components within a second range that is larger than first range.

A power mode, as referred to herein, refers to an RFID excitation energy provided by the patient monitoring system to excite the RFID component. Each RFID component, when excited, may be configured to transmit data back to the patient monitoring device such as a globally unique identification, a device specific identification, medical device identification, device serial number, programmed RFID tag data, and the like.

In low power mode, the RFID component receives RFID excitation energy when the the RFID component is held in close proximity to a RFID reader of the patient monitoring system in comparison to a high power mode. Therefore, association of an RFID component with a patient monitoring system is more likely to be intentional during low power mode. The close proximity may reduce the possibility that any given RFID component is erroneously associated with the patient monitoring system for another patient. The close proximity is relative to the larger proximity enabled in a high power mode discussed in more detail below. In other words, the low power mode may be used to associate the RFID component with a patient monitoring device within a first range. The high power mode may be used to detect the RFID component within a second range that is larger than the first range.

During the high power mode, the patient monitoring system may be configured to communicate with RFID components within a predefined range that is larger than a range associated with the close proximity required in the low power mode. If an unassociated RFID component is brought into the predefined range, the patient monitoring system may issue an alert. For example, if an ECG device is placed on an incorrect patient, the patient monitoring system for that patient may issue an alert indicating that an unassociated sensor is present within the predefined range of the patient monitoring system for that patient. The unassociated sensor may be detected as the RFID component of the sensor transmits one or more of the globally unique identification, a device specific identification, medical device identification, device serial number, programmed RFID tag data, and the like of the unassociated RFID component.

The techniques described above, and in more detail below may reduce misplacement of sensors within a medical environment. Further, as sensors themselves are becoming increasing implemented to communicate wirelessly via protocols such as Wireless Fidelity (Wifi), cellular, and the like, misplacement of sensors may become increasingly common.

It may be important to note an RFID component is embedded into sensor. For example, the RFID component may be embedded into a wireless sensor, such as a heart rate monitoring device. In some cases, a sensor itself may be configured to communicate wirelessly via their own wireless communication components. In other words, the RFID component may be an additional wireless communication component embedded in a sensor. Examples of sensors may include an electrocardiograph (ECG) sensor, a blood oxygen saturation sensor, a heart rate sensor, a blood pressure, a patient temperature sensor, other pressure sensors, and the like. Further, one or more sensors may be integrated into a single component. In any case, each discretely packaged sensor includes an embedded RFID component that is to be associated with a patient monitoring device in a first mode, and is monitored in a second mode by the patient monitoring device.

Further, it may be also important to note that an RFID component may include a passive RFID component. A passive RFID component is a RFID component without an independent power source. The passive RFID component is configured to receive and resonate energy emitted from an RFID transceiver of the patient monitoring system. A passive RFID component embedded into a wireless sensor may enable monitoring of the passive RFID component of the wireless sensor even when the wireless sensor is powered off, or has run out of power.

FIG. 1 illustrates a block diagram illustrating a computing system configured to monitor wireless components. The computing system 100 may include a patient monitoring device 101 having a processor 102, a storage device 104, a memory device 106, a network interface 108, and a display interface 110. The patient monitoring device 101 may communicate, via the network interface 108, with one or more sensors 114.

The storage device 104 may be a non-transitory computer-readable medium having a RFID operation module 116. The RFID operation module 116 may be implemented as logic, at least partially comprising hardware logic, as firmware embedded into a larger computing system, or any combination thereof. The RFID operation module 116 is configured to enter a low power mode to associate an RFID component 118 of a sensor 114 with the patient monitoring device 101 within a first range. The RFID operation module 116 may also enter a high power mode wherein the patient monitoring device 101 is to detect the RFID component 118 within a second range of the patient monitoring device 101, wherein the second range is larger than the first range.

The processor 102 may be a main processor that is adapted to execute the stored instructions. The processor 102 may be a single core processor, a multi-core processor, a computing cluster, or any number of other configurations. The processor 102 may be implemented as Complex Instruction Set Computer (CISC) or Reduced Instruction Set Computer (RISC) processors, x86 Instruction set compatible processors, multi-core, or any other microprocessor or central processing unit (CPU).

The memory device 106 can include random access memory (RAM) (e.g., static RAM, dynamic RAM, zero capacitor RAM, Silicon-Oxide-Nitride-Oxide-Silicon, embedded dynamic RAM, extended data out RAM, double data rate RAM, resistive RAM, parameter RAM, etc.), read only memory (ROM) (e.g., Mask ROM, parameter ROM, erasable programmable ROM, electrically erasable programmable ROM, etc.), flash memory, or any other suitable memory systems. The main processor 102 may be connected through a system bus 120 (e.g., PCI, ISA, PCI-Express, etc.) to the network interface 108. The network interface 108 may enable the patient monitoring device 101 to communicate with the one or more sensors 118, as indicated by the dashed line 120. The dashed line 120 is intended to indicate that the sensors 114 may hardwired to the patient monitoring device 101, or may be configured to wirelessly communicate with the patient monitoring device 101 using a wireless protocol such as Wifi, cellular data protocols, Bluetooth protocols, Zigbee® or derivative protocols, and the like, as indicated at 122. In either the wired or wireless case, each sensor 114 includes an RFID component 118.

The sensors 114 may each include an RFID component 118 configured to communicate with an RFID transceiver 124, as indicated at 126. The RFID transceiver 124 may send and receive signals. For example, the RFID 124 is configured to send a signal to the RFID component 118 and read a response from the RFID component. In some cases, the RFID transceiver 124 is configured as an RFID reader wherein an encoded radio signal is transmitted from the RFID transceiver 124 to the RFID component 118. The radio signal may be transmitted during low power mode, or high power mode, as determined by the RFID operation module.

As discussed above, the low power mode implemented by the RFID operation module 116 may reduce unintentional association of a given sensor 114 with the patient monitoring device 101 by enabling association of an RFID component 118 within a first range that is smaller than the second range. In high power mode, the RFID transceiver 124 may transmit a signal having a higher range than a signal associated with low power mode. The high power mode enables the patient monitoring device 101 monitor RFID components 118 within the second range of the patent monitoring device 101, including detecting when an unassociated RFID component is present within the second range.

In embodiments, the patient monitoring device 101 may render images at a display device 128, via the display interface 110. The display device 128 may be an integrated component of the patient monitoring device 101, a remote component such as an external monitor, or any other configuration enabling the patient monitoring device 101 to render a graphical user interface. As discussed in more detail below, a graphical user interface rendered at the display device 108 may be used to display information to a user of the patient monitoring device 101. For example, the display device 128 may be used to render a warning when an unassociated RFID component is detected within the second range of the high power mode.

The block diagram of FIG. 1 is not intended to indicate that the patient monitoring device 101 is to include all of the components shown in FIG. 1. Further, the patient monitoring device 101 may include any number of additional components not shown in FIG. 1, depending on the details of the specific implementation.

Figure 2:
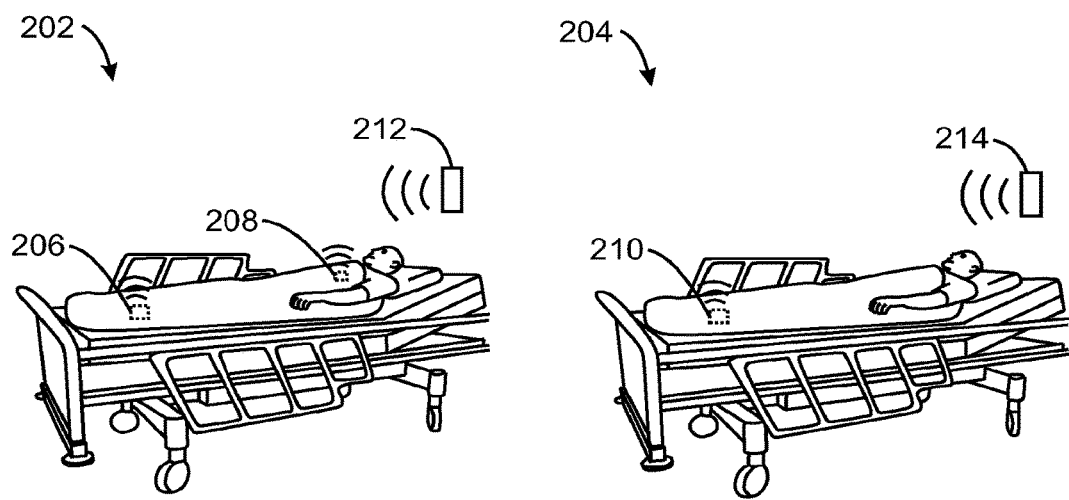
FIG. 2 illustrates a diagram of a system monitoring wireless component in a medical environment.

FIG. 2 illustrates a diagram of a system monitoring wireless component in a medical environment. In some cases, a medical environment 200 may include more than one patient, such as a first patient 202 and a second patient 204 indicated in FIG. 2. The first patient 202 and the second patient 204 may be in close proximity to each other. In this scenario, sensors associated with the first patient 202 may be accidentally placed on the second patient 204.

For example, the first patient 202 may be wearing an ECG sensor 206 and a pressure sensor 208, while the second patient 204 may only be wearing a pressure sensor 210. If the ECG sensor 206 from the first patient 202 is dropped and mistakenly applied to the second patient 204, inaccurate ECG measurements may be recorded by a patient monitoring device 212 associated with the first patient 202, but not the second patient 204. Further, a medical mistake may occur if the second patient 204, while wearing the ECG sensor 206, enters cardiac arrest. In this case, a clinician may mistakenly engage in medical aid including automatic external defibrillation on the first patient, rather than the second patient.

The techniques described herein include detecting an unassociated sensor via RFID communication. In the example above, if the ECG sensor 208 is missing, a patient monitoring device 212 may issue an alert, such as a sound, a message, and the like, indicating that the ECG sensor 208 is not present within the second range of the patient monitoring device 212. In some cases, a second patient monitoring device 214 may issue an alert if the ECG sensor 208 is within a predefined range of the patient monitoring device 214. Therefore, the techniques described herein may be used to find misplaced items, as well as preventing incorrect medical care when sensors are incorrectly placed on a given patient. Further, in the case where a given sensor is a wireless sensor with a dead battery, the RFID component may continue to communicate with a patient monitoring device since the RFID component of the sensor may not require an independent battery source to operate. Therefore, sensors having dead batteries may be located if they are within the predefined area, or second range, of an associated patient monitoring device, or if they are within a predefined area or range of an unassociated patient monitoring device.

Figure 3:
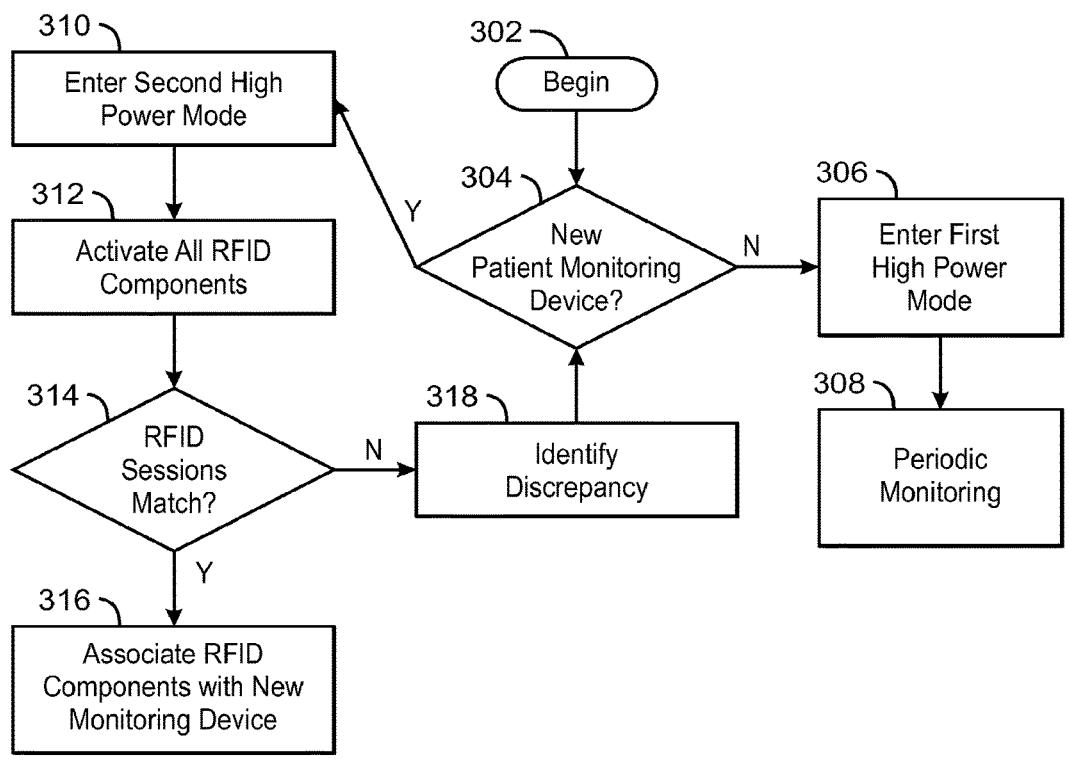
FIG. 3 illustrates a process flow diagram illustrating various modes of monitoring wireless components.

FIG. 3 illustrates a process flow diagram illustrating various modes of monitoring wireless components. In some cases, a patient may need to be associated with a new patient monitoring device, such as the patient monitoring device 101 of FIG. 1. For example, a patient may be moved or transferred to another area of a hospital, to a new hospital, and the like. In this scenario, a new patient monitoring device may be associated with any sensors via embedded RFID tags within each sensor for the given patient. In these scenarios, the high power mode discussed above in reference to FIG. 1 and FIG. 2 may be referred to herein as the first high power mode.

The process 300 may begin at 302. At 304, the process 300 may determine whether a new patient monitoring device is being used. If not, the process 300 may continue in the first high power mode at 306, assuming that RFID components have been previously associated with the current patient monitoring device in low power mode discussed above in reference to FIG. 1 and FIG. 2. In embodiments, the first high power mode is performed in periodic intervals. For example, an RFID transceiver, such as the RFID transceiver 124 may be configured to read all RFID components within the predetermined range once per minute.

If a new patient monitoring device is detected at 304, a second high power mode is entered at 310. In the second high power mode, all RFID components are activated 312 by the RFID transceiver 124 issuing a high power signal, and RFID component sessions are read. At block 314, if the RFID component sessions match the RFID component sessions previously associated with the old patient monitoring device, then the RFID components are associated with the new monitoring device at block 316. If, at block 314, the RFID component sessions do not match, then any discrepancy is identified at 318, and the process 300 continues at 304 until all RFID component sessions are matched. The process 300 including the second high power mode enables a quick association of sensors with a new monitor. In other words, the RFID components for each sensor may be re-associated with the new monitor in one action that a user can confirm.

Figure 4:
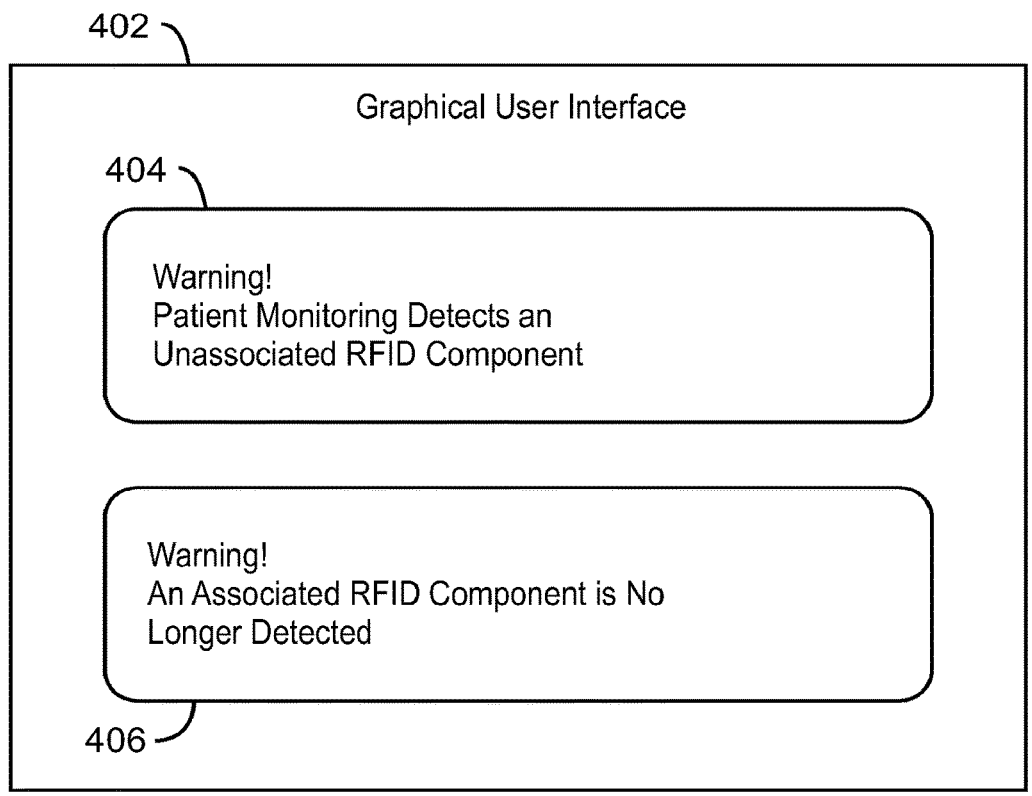
FIG. 4 illustrates a graphical user interface to render a warning related to monitoring wireless components.

FIG. 4 illustrates a graphical user interface to render a warning related to monitoring wireless components. As discussed above in regard to FIG. 2, warnings may be issued when unassociated RFID components are detected within a range of a patient monitoring device. In some embodiments, warnings are issued via a graphical user interface 402 rendered at a display device, such as the display device 128.

For example, if an unassociated RFID component is detected within the range of the patient monitoring device, a warning 404 may be displayed on the graphical user interface 402. As another example, if an associated RFID component is no longer detected, a warning 406 may be rendered. The warnings illustrated in FIG. 4 are examples, and alarm other formats are considered, such as an audible alarm, a light, or any other alarm that may be used to indicate a potential problem with RFID components being associated with an incorrect patient, and/or patient monitoring device.

Figure 5:
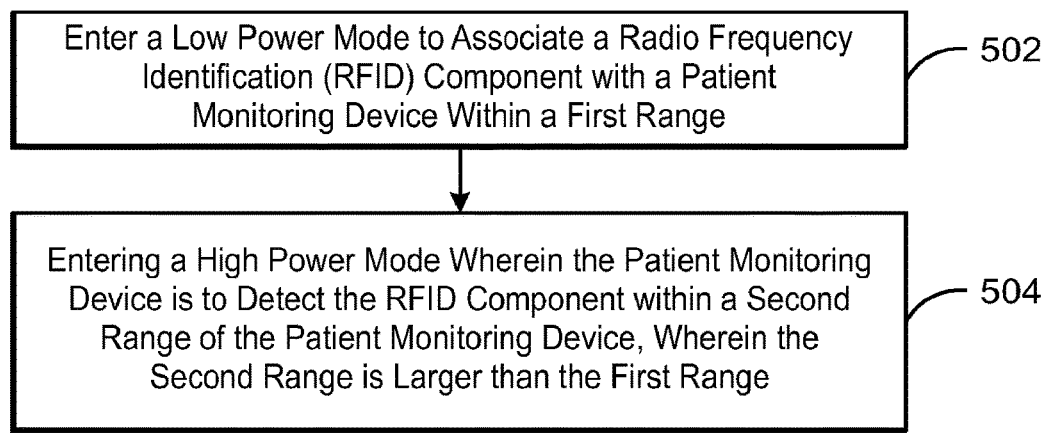
FIG. 5 is a block diagram illustrating a method of monitoring wireless components.

FIG. 5 is a block diagram illustrating a method of monitoring wireless components. At 502, a low power mode to associate a radio frequency identification (RFID) component with a patient monitoring device within a first range is entered. At block 504, a high power mode is entered. In the high power mode, the patient monitoring device is to detect the RFID component within a second range of the patient monitoring device, wherein the second range is larger than the first range.

The method 500 may include additional steps. For example, monitoring may include periodic wireless signal transmissions from the patient monitoring device to the RFID component. Further, the method 500 may include issuing a warning when the associated RFID component is not detected within the second range, as discussed above in regard to FIG. 4. In some cases, the method 500 may include issuing a warning when a second RFID component is detected within the second range that has not been associated with the patient monitoring.

In some cases, a sensor may have simply been misplaced. Therefore, the method 500 may include providing an indication of a presence of an RFID component within the second range upon receiving a user request. In this manner, a user may determine that a missing sensor is still within range of the patient monitoring device.

Figure 6:
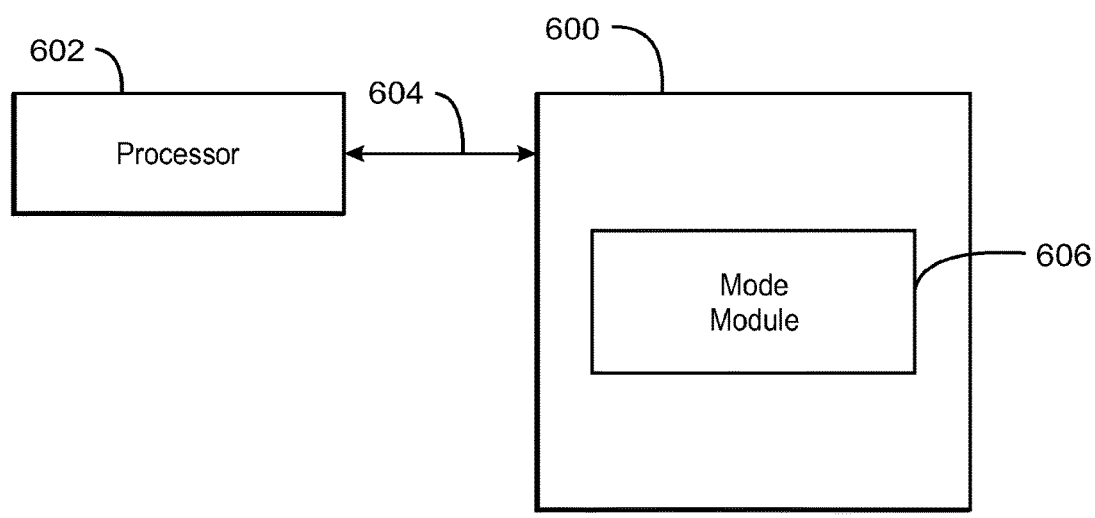
FIG. 6 is a block diagram of a computer readable medium that includes modules for monitoring wireless components.

FIG. 6 is a block diagram of a computer readable medium that includes modules for monitoring wireless components. The computer readable medium 600 may be a non-transitory computer readable medium, a storage device configured to store executable instructions, or any combination thereof. In any case, the computer-readable medium is not configured as a carry wave or a signal.

The computer-readable medium 600 includes code adapted to direct a processor 602 to perform actions. The processor 602 accesses the modules over a system bus 604.

A mode module 606 may be configured to enter a low power mode to associate a radio frequency identification (RFID) component with a patient via a patient monitoring device within a first range. The mode module 606 may also be configured to enter a high power mode wherein the patient monitoring device is to detect the RFID component within a second range of the computerized patient monitor, wherein the second range is larger than the first range.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the techniques described herein, including the best mode, and also to enable any person skilled in the art to practice the techniques described herein, including making and using any devices or systems and performing any incorporated methods. The patentable scope of the techniques described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient monitoring system comprising:
one or more physiological sensors acquiring physiological parameter data from a patient, each physiological sensor having a radio frequency identification (RFID) component embedded therein; and
a patient monitoring device comprising:
a RFID transceiver to transmit and receive wireless signals to and from the RFID component;
a processor;
an RFID operation module executable on the processor to operate the patient monitoring device in modes comprising:
a low power mode wherein the RFID transceiver communicates with one or more RFID components within a predefined first distance range of the patient monitor and associates the one or more RFID components with the patient monitoring device; and
a high power mode wherein the patient monitoring device detects the RFID component within a predefined second distance range of the patient monitoring device, wherein the second distance range is larger than the first distance range;
wherein no new physiological sensor is permitted to be associated with the patient monitoring device during operation in the high power mode; and
wherein the patient monitoring device only records physiological parameter data from the one or more physiological sensors associated with the patient monitoring device.

2. The system of claim 1, wherein the RFID operation module is further configured to monitor the one or more associated RFID components via periodic wireless signal transmissions from the patient monitoring device to the RFID component.

3. The system of claim 1, wherein the RFID operation module is further configured to issue a warning when the associated RFID component is not detected within the predefined second distance range.

4. The system of claim 1, wherein the RFID component is a first RFID component, and wherein the RFID operation module is further configured to issue an unassociated sensor warning when a second RFID component is detected within the predefined second distance range that has not been associated with the patient monitoring device.

5. The system of claim 1, wherein the RFID component does not include an independent power source.

6. The system of claim 1, wherein the RFID operation module is further configured to provide an indication of a presence of the RFID component within the predefined second distance range upon receiving a user request.

7. The system of claim 1, wherein the high power mode is a first high power mode; and wherein the RFID operation module is further configured to enter a second high power mode wherein the one or more associated RFID components are re-associated with the patient monitoring device.

8. A method for controlling a patient monitoring system, the method comprising:
determining that a physiological sensor is to be associated with a patient monitoring device, the physiological sensor containing a radio frequency identification (RFID) component and the patient monitor containing an RFID transceiver;

entering a low power mode with the RFID transceiver to associate a radio frequency identification (RFID) component in the physiological sensor with the patient monitoring device when the physiological sensor is within a predefined first distance range of the patient monitoring device; and entering a high power mode with the RFID transceiver wherein the patient monitoring device detects RFID components from one or more physiological sensors within a predefined second distance range of the patient monitoring device, wherein the second distance range is larger than the first distance range;

wherein no new physiological sensor is permitted to be associated with the patient monitoring device during operation in the high power mode; and recording physiological parameter data only from the one or more physiological sensors associated with the patient monitoring device.

9. The method of claim 8, further comprising monitoring the one or more associated RFID components via periodic wireless signal transmissions from the patient monitoring device to the respective RFID component.

10. The method of claim 8, further comprising issuing a warning when the associated RFID component is not detected within the predefined second distance range.

11. The method of claim 8, wherein the RFID component of the associated physiological sensor is a first RFID component, further comprising:
detecting a second RFID component within the predefined second distance range that has not been associated with the patient monitoring device; and
issuing an unassociated sensor warning.

12. The method of claim 11, further comprising operating the patient monitor to record health parameter data from the associated physiological sensor and not record health parameter data from an unassociated physiological sensor containing the second RFID component.

13. The method of claim 8, further comprising providing an indication of a presence of the RFID component within the predefined second distance range upon receiving a user request.

14. The method of claim 8, wherein the high power mode is a first high power mode, and further comprising entering a second high power mode wherein the RFID component is re-associated with the patient monitoring device.

15. A method for controlling a patient monitoring system, the method comprising:
determining that one or more physiological sensors is to be associated with a first patient monitoring device, each physiological sensor containing a radio frequency identification (RFID) component and the first patient monitor containing an RFID transceiver;
placing the physiological sensors into a predefined first distance range of the first patient monitoring device;
entering a low power mode with the RFID transceiver to associate the RFID component in each of the physiological sensors within the predefined first distance range with the first patient monitoring device; and
entering a first high power mode with the RFID transceiver wherein the first patient monitoring device detects RFID components from physiological sensors within a predefined second distance range of the first patient monitoring device, wherein the second distance range is larger than the first distance range;
wherein no new physiological sensor is permitted to be associated with the first patient monitoring device during operation in the first high power mode; and
recording physiological parameter data only from the physiological sensors associated with the first patient monitoring device.

16. The method of claim 15, further comprising:
detecting a new patient monitoring device, the new patient monitoring device having a new RFID transceiver;
entering a second high power mode to associate the RFID components associated with the first patient monitoring device with the new patient monitoring device.

17. The method of claim 16, further comprising, in the second high power mode:
activating all RFID components in physiological sensors within a third predetermined range of the new patient monitoring device;
detecting the activated RFID components at the new RFID transceiver in the new patient monitor;
comparing the detected activated RFID components with the RFID components associated with the first patient monitoring device; and
confirming complete association transfer when the detected activated RFID components are the same as the RFID components associated with the first patient monitoring device.

18. The method of claim 15, further comprising issuing a warning when one or more of the associated RFID components is not detected within the predefined second distance range.

19. The method of claim 15, further comprising issuing a warning when an RFID component is detected within the predefined second distance range that has not been associated with the patient monitoring device.

20. The method of claim 15, further comprising providing an indication of a presence of one or more of the RFID components within the predefined second distance range upon receiving a user request.

* * * * *